(12) United States Patent
Lee et al.

(10) Patent No.: US 11,116,949 B2
(45) Date of Patent: Sep. 14, 2021

(54) DRAINAGE TUBE INTRODUCER

(71) Applicant: WOO YOUNG MEDICAL CO., LTD., Chungcheonbuk-do (KR)

(72) Inventors: Young Gyu Lee, Seoul (KR); Hyeon Jeong Park, Cheongju-si (KR)

(73) Assignee: WOO YOUNG MEDICAL CO., LTD.

( * ) Notice: Subject to any disclaimer, the term of this patent is extended or adjusted under 35 U.S.C. 154(b) by 496 days.

(21) Appl. No.: 16/240,952

(22) Filed: Jan. 7, 2019

(65) Prior Publication Data

US 2019/0151633 A1 May 23, 2019

Related U.S. Application Data (63) Continuation of application No. PCT/KR2017/007774, filed on Jul. 19, 2017.

(30) Foreign Application Priority Data

Jul. 22, 2016 (KR) .......................... 10-2016-0093536

(51) Int. Cl.
*A61M 27/00* (2006.01)
*A61B 17/00* (2006.01)
(Continued)

(52) U.S. Cl.
CPC .............. *A61M 27/00* (2013.01); *A61B 17/00* (2013.01); *A61B 17/50* (2013.01); *A61M 1/00* (2013.01);
(Continued)

(58) Field of Classification Search
CPC ... A61F 11/002; A61M 27/002; A61M 27/00; A61M 25/0102; A61M 25/02; A61M 39/0247
See application file for complete search history.

(56) References Cited

U.S. PATENT DOCUMENTS 3,948,271 A * 4/1976 Akiyama .............. A61F 11/002
604/540
6,527,780 B1 * 3/2003 Wallace ........... A61B 17/12022
606/1
(Continued)

FOREIGN PATENT DOCUMENTS

EP 1371382 A1 12/2003
EP 2452709 A2 5/2012
(Continued)

OTHER PUBLICATIONS

Chinese Office Action (CN201780038424.9), CNIPA, dated Aug. 27, 2020.
(Continued)

*Primary Examiner* — Catharine L Anderson
*Assistant Examiner* — Arjuna P Chatrathi
(74) *Attorney, Agent, or Firm* — Park & Associates IP Law, P.C.

(57) ABSTRACT

The present invention provides a drainage tube introducer wherein while a drainage tube is fitted over an introducing end portion (42) protruding through a pin hole (32) and is introduced through an incision portion (4) into an infected portion (2) in cooperation with the introducing end portion (42), a stop block (52) is pressed by pushing a sleeve (70) frontward, which bends an operating lever (50) made of an elastic material to release the stop block (52) from a stop hole (38). Accordingly, a pin (40) is moved rearward by an elastic member (60) to withdraw the introducing end portion (42) protruding through the pin hole and to separate the drainage tube introduced into the infected portion (2) from the introducing end portion (42).

7 Claims, 11 Drawing Sheets

(51) Int. Cl.
*A61M 25/01* (2006.01)
*A61M 25/02* (2006.01)
*A61M 39/02* (2006.01)
*A61M 1/00* (2006.01)
*A61B 17/50* (2006.01)

(52) U.S. Cl.
CPC ........ *A61M 25/0102* (2013.01); *A61M 25/02* (2013.01); *A61M 39/0247* (2013.01); *A61M 2025/0233* (2013.01); *A61M 2039/0261* (2013.01); *A61M 2039/0276* (2013.01); *A61M 2210/1475* (2013.01)

(56) References Cited

U.S. PATENT DOCUMENTS

| | | | |
|---|---|---|---|
| 8,945,142 B2* | 2/2015 | Schaeffer | A61B 17/3423 606/108 |
| 9,155,656 B2* | 10/2015 | Schaller | A61F 9/0017 |
| 2008/0188833 A1 | 8/2008 | Taufig | |
| 2011/0009873 A1 | 1/2011 | Schraga | |
| 2012/0109111 A1 | 5/2012 | Li | |
| 2013/0281817 A1 | 10/2013 | Schaller et al. | |
| 2014/0088360 A1 | 3/2014 | Kawaura | |

FOREIGN PATENT DOCUMENTS

| | | |
|---|---|---|
| EP | 2727621 A1 | 5/2014 |
| JP | 4159559 B2 | 10/2008 |
| JP | 2015-516858 A | 6/2015 |
| JP | 2016-013436 A | 1/2016 |
| KR | 20-2008-0003156 U | 8/2008 |
| KR | 10-1377324 B1 | 3/2014 |
| WO | 2004000396 A1 | 12/2003 |
| WO | 2012137863 A1 | 10/2012 |

OTHER PUBLICATIONS

European Search Report (EP 17831349.0), EPO, dated Dec. 16, 2019.
International Search Report (PCT/KR2017/007774), WIPO, dated Dec. 6, 2017.
Korean Office Action (KR 10-2016-0093536), KIPO, dated Dec. 18, 2017.
Korean Decision to Grant (KR 10-2016-0093536), KIPO, dated Sep. 17, 2018.

* cited by examiner

DRAINAGE TUBE INTRODUCER

REFERENCE TO RELATED APPLICATIONS

This is a continuation of International Patent Application PCT/KR2017/007774 filed on Jul. 19, 2017, which designates the United States and claims priority of Korean Patent Application No. 10-2016-0093536 filed on Jul. 22, 2016, the entire contents of which are incorporated herein by reference.

FIELD OF THE INVENTION

The present invention relates to a drainage tube used to treat a Bartholin's duct abscess occurring mostly in a woman's Bartholin's duct. More particularly, the present invention relates to a drainage tube introducer for operating on a Bartholin's duct abscess, the introducer used to insert a drainage tube into an infected portion.

BACKGROUND OF THE INVENTION

A Bartholin's duct abscess, which is a disease occurring in women, refers to an expansion of a Bartholin's duct occurring when an abscess (a pus pocket) is formed due to infections or damage occurring in the Bartholin's duct, which releases mucus secreted from a Bartholin's gland positioned at an entrance side of a vagina of a woman. When the Bartholin's duct is blocked, the Bartholin's duct may be expanded up to 3 cm to 5 cm or at least 5 cm in diameter.

Generally, a Bartholin's duct abscess is treated by marsupialization or incision. The marsupialization of a Bartholin's duct abscess is a surgical technique of cutting a drainage slit into the abscess such that pus is drained therefrom. The incision of the Bartholin's duct abscess, which is mostly performed when an abscess is recurrent despite marsupialization, is a treatment to remove the entirety of the Bartholin's duct abscess.

Generally, the marsupialization of a Bartholin's duct abscess is performed under anesthesia in an operating room, and as treatment time often increases, a patient occasionally awakes from the anesthesia. Accordingly, an additional anesthetic drug is applied to the patient, which may endanger the life of the patient. Furthermore, when a motion of the patient happens during the treatment, performing the treatment is difficult. In addition, the drainage slit formed during the treatment often blocks in the process of restoration after the treatment and thus the Bartholin's duct abscess recurs frequently. When the Bartholin's duct abscess recurs, the incision of the Bartholin's duct abscess is required to be performed, which takes a relatively long time for treatment and recovery.

Accordingly, a way to efficiently treat a Bartholin's duct abscess is required urgently.

SUMMARY OF THE INVENTION

An embodiment of the present invention is intended to propose a drainage tube and an introducer of the same, wherein the introducer is advantageous in terms of an efficiency improvement of a treatment of draining pus out of an infected abscess.

A technical problem to be solved is not limited to the technical problem mentioned herein, and other technical problems not mentioned herein will be clearly understood by one of ordinary skill in the art from descriptions below.

In order to accomplish the above object, the present invention provides a drainage tube introducer, including: an introducer body including a pin hole provided on a distal end thereof, an inner space communicating with the pin hole, and a stop hole formed through one side of a circumference of the introducer body, the stop hole communicating with the inner space; a pin for inserting a drainage tube, the pin being introduced to the inner space so as to move forward/rearward relative to the pin hole, wherein when the pin moves forward, an introducing end portion of a distal end side of the pin protrudes through the pin hole to an outside; an operating lever, made of an elastic material, being connected to a rear portion of the pin for inserting the drainage tube and having a stop block inserted into the stop hole while the pin moves forward, wherein when the stop block is pressed, the stop block is bent in a direction being released from the stop hole; and an elastic member applying an elastic force to the pin in a direction in which the pin moves rearward.

Here, the drainage tube may be fitted over an outer circumference of the introducing end portion protruding through the pin hole to the outside, be introduced through an incision portion into an infected portion in cooperation with the introducing end portion, and be separated from the introducing end portion when the stop block is released from the stop hole and the pin is moved rearward by the elastic member.

The stop block may include a protruding part protruding through the stop hole to an outside. A middle portion of the protruding part may be configured to protrude more than the surrounding portions.

The stop block may include a stopping part provided on a rear portion thereof, the stopping part including a first surface being in contact with an inner circumference of the stop hole and a second surface extending rearward from the first surface and being in contact with a wall surface of the inner space.

The drainage tube introducer according to an embodiment of the present invention may further include: a sleeve for manipulating the pin, the sleeve being fitted over the outer circumference of the introducer body so as to move slidably thereon and arranged so as to cover the stop hole and having a pressing protrusion pressing the protruding part while being in contact with the protruding part when the sleeve slides.

The drainage tube introducer according to the embodiment of the present invention may further include: a position determination means determining a position of the sleeve on the introducer body such that the sleeve is positioned at a position to cover the stop hole.

The drainage tube introducer according to the embodiment of the present invention may further include: a pin guide guiding a movement of the pin forward and rearward.

The drainage tube introducer according to the embodiment of the present invention may further include: an insertion hole cover being separably combined with a proximal end of the introducer body, wherein a pin insertion hole communicating with the inner space may be provided at the proximal end of the introducer body.

The drainage tube introducer according to the embodiment of the present invention may further include: a cap being fitted over a distal end side of the introducer body, the cap protecting the introducing end portion protruding through the pin hole to the outside and the drainage tube being fitted over the outer circumference of the introducing end portion.

The technical solution described above will be understood more in detail and clearly by the embodiment described below and the accompanying drawings. In addition, apart from the technical solution mentioned above, various technical solutions may be presented additionally below.

As described above, according to the embodiment of the present invention, after the drainage tube is fitted over the introducing end portion protruding through the pin hole, the drainage tube is inserted through the incision portion into an infected abscess (may be a Bartholin's duct abscess) in cooperation with the introducing end portion, and when the stop block is pressed down and released from the stop hole, the pin is moved rearward by the elastic member and the protruded introducing end portion is withdrawn into the introducer body, and when the drainage tube is separated from the introducing end portion, the insertion of the drainage tube is completed, whereby the abscess treatment can be performed simply and rapidly, and a size of the incision portion can be minimized. Accordingly, the treatment may be performed outside of an operating room under local anesthesia, and when the treatment is performed in an operating room, anesthesia time may be decreased so as to considerably reduce the anxiety of a patient.

The drainage tube inserted into the infected abscess during the treatment may prevent a drainage slit from being blocked (treatment failure) in the process of recovery after the treatment.

DETAILED DESCRIPTION OF THE INVENTION

Hereinbelow, an exemplary embodiment of the present invention will be described with reference to the accompanying drawings.

A drainage tube and a drainage tube introducer for operating on a Bartholin's duct abscess according to the embodiment of the present invention may be used in treatment of various abscesses. For example, in relation to the treatment of a Bartholin's duct abscess, the drainage tube and the drainage tube introducer may be used in a treatment forming a drainage slit (an exit) through which pus is discharged from the abscess while a treatment portion of the infected Bartholin's duct abscess is recovered, through which mucus from Bartholin's gland is discharged after the treatment is recovered.

Figure 1:
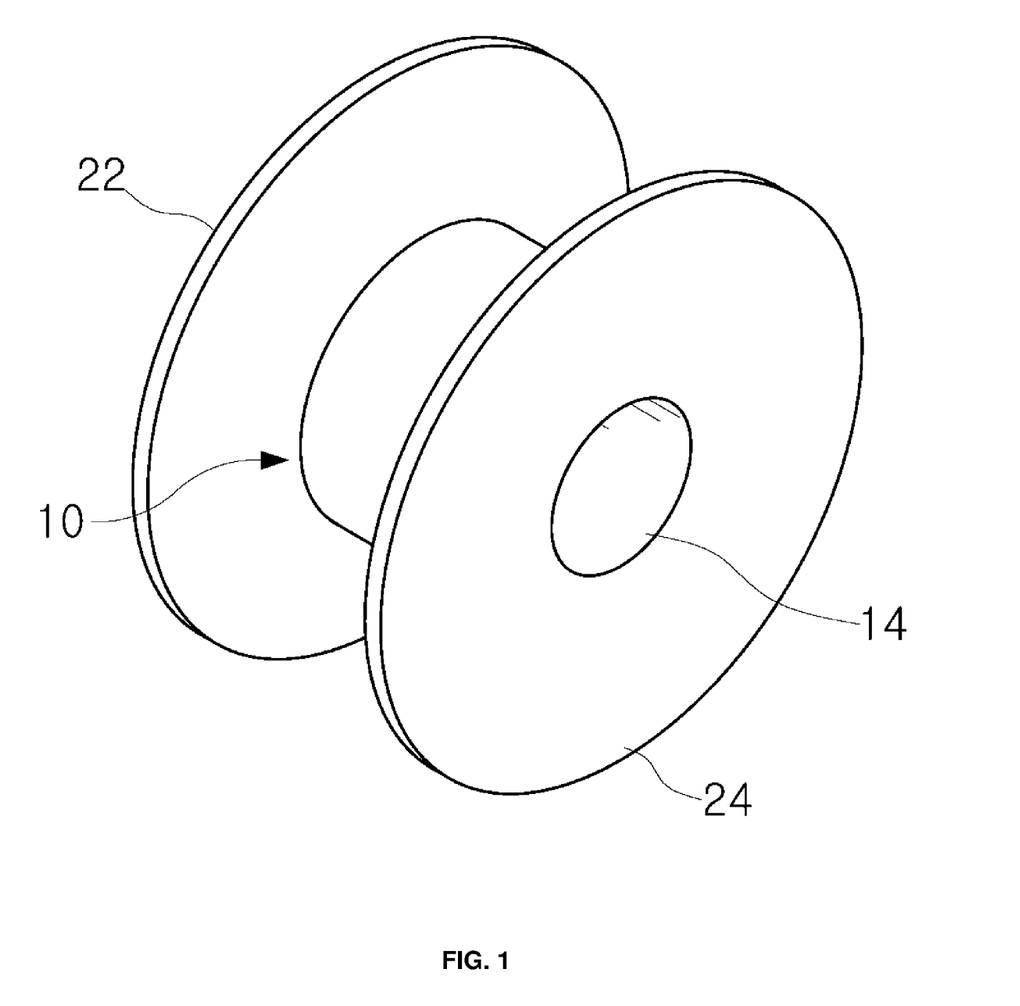
FIG. 1 is a perspective view showing a drainage tube according to an embodiment of the present invention.
Figure 2:
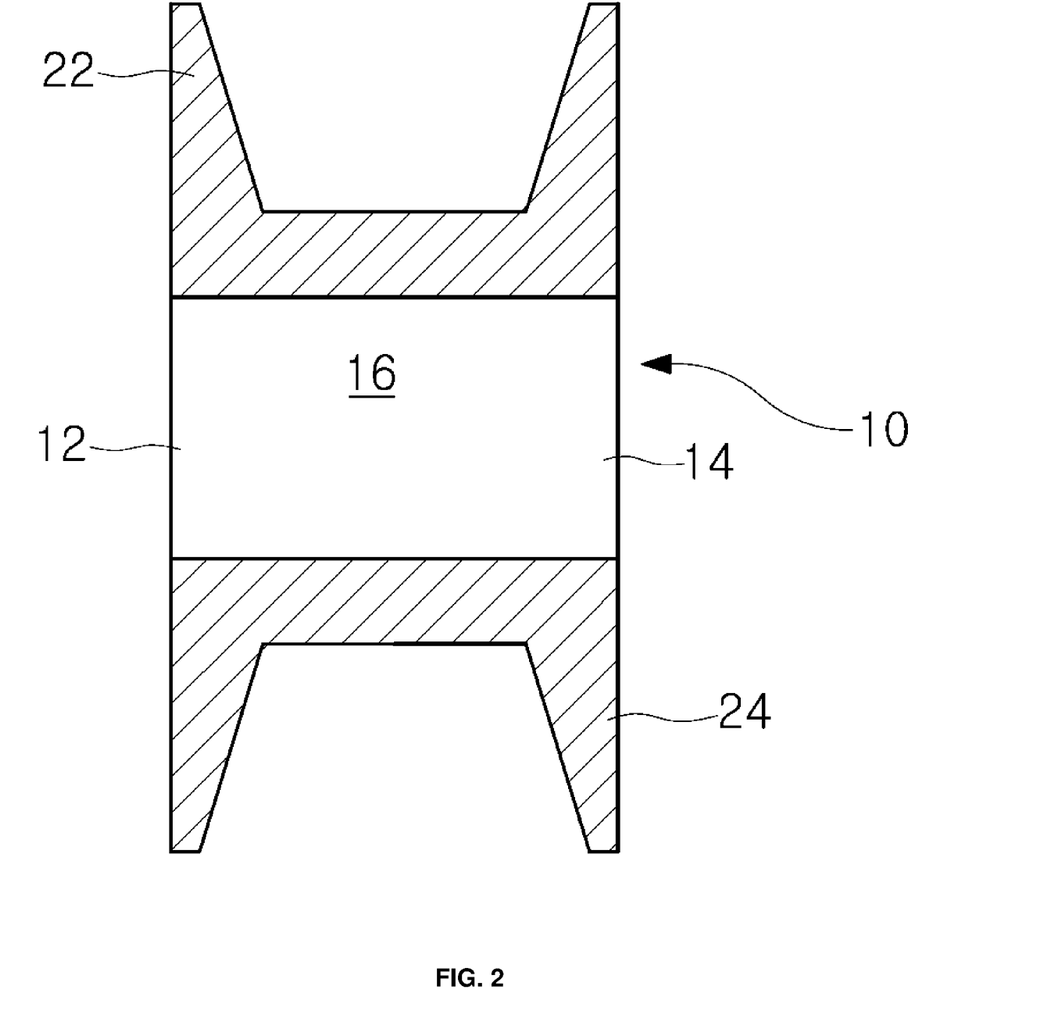
FIG. 2 is a cross-sectional view showing the drainage tube according to the embodiment of the present invention.
Figure 3:
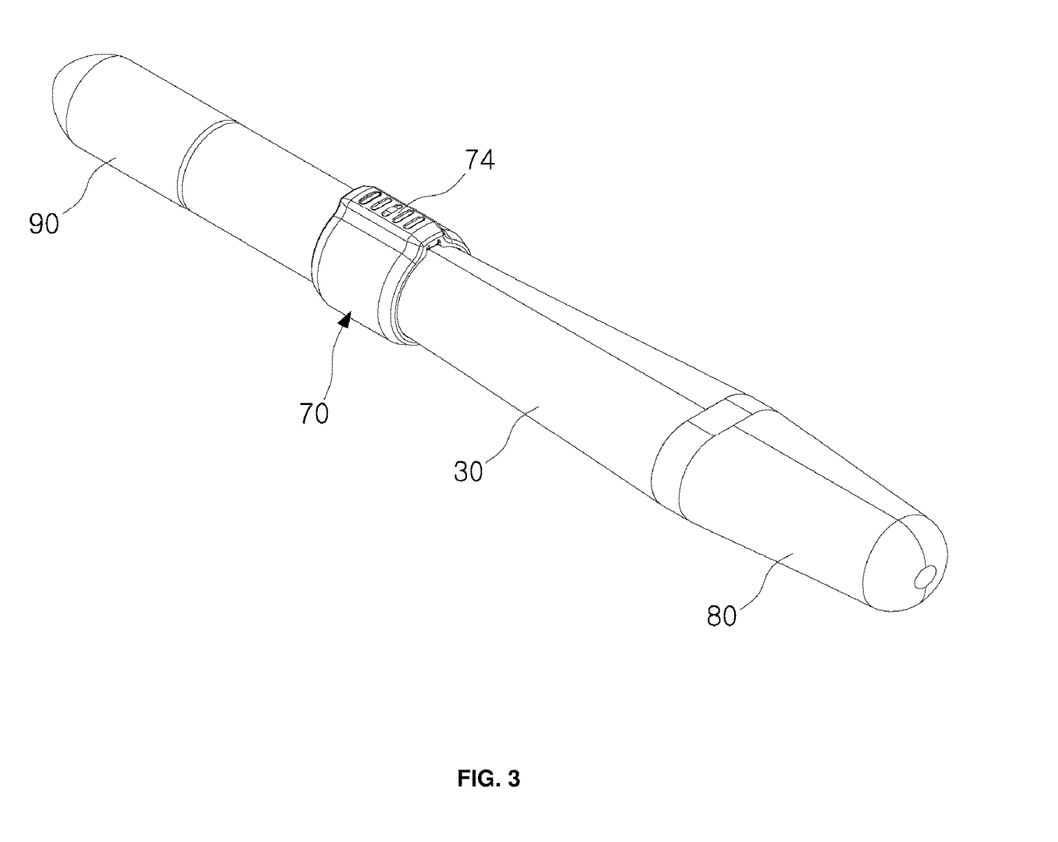
FIGS. 3 and 4 are perspective views showing a drainage tube introducer for operating on a Bartholin's duct abscess according to the embodiment of the present invention.
Figure 4:
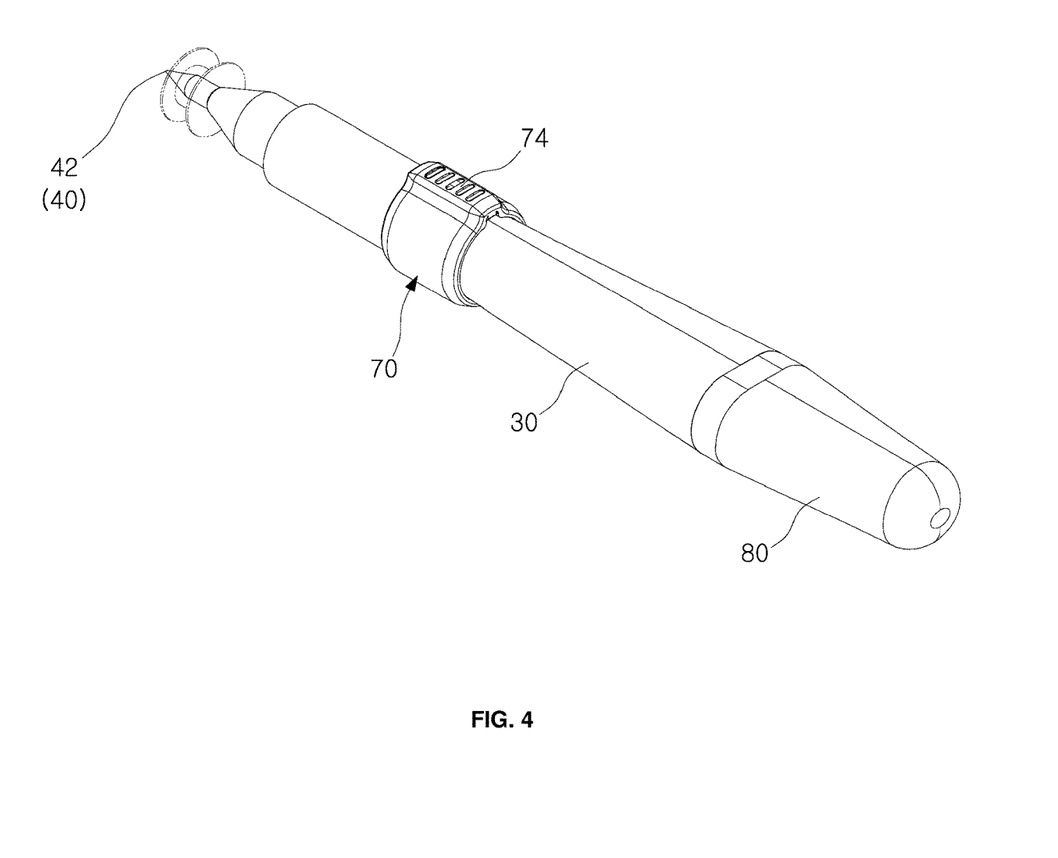
Figure 5:
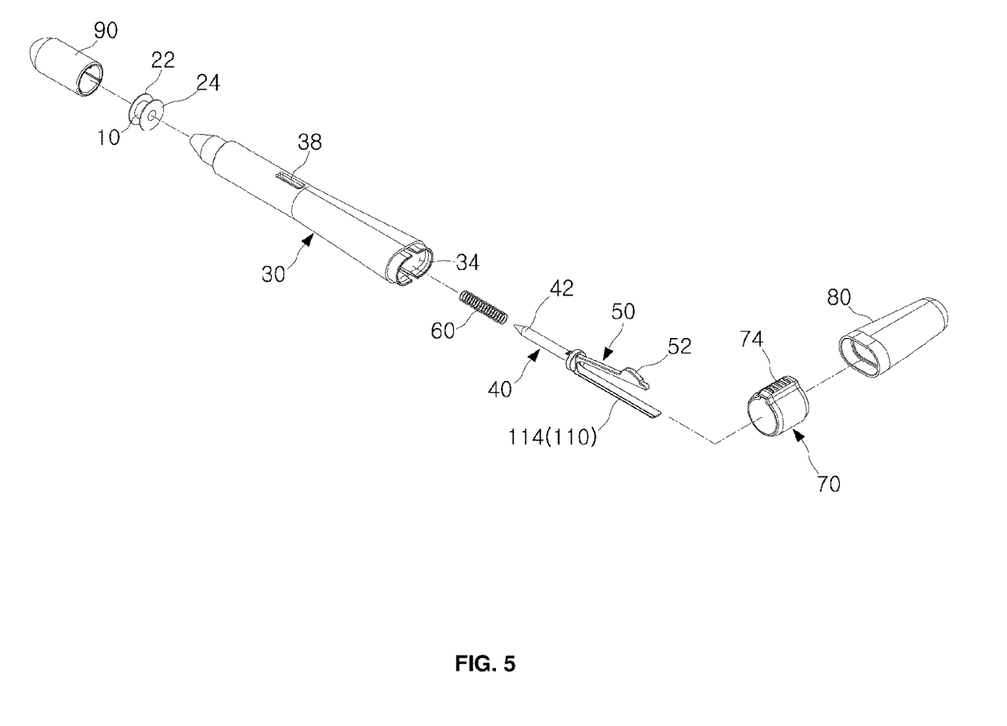
FIG. 5 is an exploded perspective view showing the drainage tube introducer according to the embodiment of the present invention.

The drainage tube according to the embodiment of the present invention is shown in FIGS. 1 and 2.

As shown in FIGS. 1 and 2, the drainage tube according to the embodiment of the present invention includes a tube-shaped tube member 10 having a predetermined length, and a first wing member 22 and a second wing member 24 arranged on each of opposite sides of the tube member 10 in a longitudinal direction thereof.

The tube member 10 includes a first end portion 12 and a second end portion 14 constituting each of open opposite ends of the tube member 10 in the longitudinal direction thereof, and a drainage passage 16, which is in an inner part of the tube member 10, arranged between the first end portion 12 and the second end portion 14 at the opposite sides. The drainage passage 16 communicates with the first end portion 12 and the second end portion 14 at the opposite sides each other. A cross-section of the tube member 10 may have a shape such as a circle, an oval, or a polygon.

As for the tube member 10, a side of the first end portion 12 is inserted through an incision portion (see a reference numeral 4 of FIG. 11) formed by incision at the infected abscess (may be the Bartholin's duct abscess) (see a reference numeral 2 of FIG. 11) into the infected portion, and while the incision portion, which is the treatment portion, is recovered, pus secreted from the infected portion is introduced through the first end portion 12 into the drainage passage 16, and the pus introduced into the drainage passage 16 is through the second end portion 14 discharged to an outside of the infected portion.

Both of the first wing member 22 and the second wing member 24 have structures protruding in outer side directions of the tube member 10. The first wing member 22 is provided on an outer circumference of the first end portion 12 of the tube member 10, and the second wing member 24 is provided on an outer circumference of the second end portion 14 of the tube member 10. The first wing member 22 and the second wing member 24 may be configured to have a shape of an edge of a circle, an oval, or a polygon. In addition, each of the first wing member 22 and the second wing member 24 may be configured to include a plurality of unit wings. The first wing member 22 and the second wing member 24 may have shapes or configurations different from each other.

The first wing member 22 is inserted into the infected abscess in cooperation with the first end portion 12 of the tube member 10 and prevents the tube member 10 from being removed from the infected portion by a holding function of the first wing member. The second wing member 24 restricts an insertion depth of the tube member 10 into the infected abscess by a holding function of the second wing member. A state at which the second end portion 14 of the tube member 10 inserted into the infected portion is exposed to the outside of the infected portion is maintained by the holding function of the second wing member 24.

Preferably, the tube member 10, the first wing member 22, and the second wing member 24 are integrally configured. Furthermore, the tube member 10, the first wing member 22, and the second wing member 24 are preferably made of a medical silicon or synthetic resins having a predetermined elasticity.

Meanwhile, unlike the above description, in the drainage tube according to the embodiment of the present invention, the second end portion 14 of the tube member 10 is inserted into the infected abscess and the first end portion 12 may be exposed to the outside of the infected portion.

The configuration and operation relation of the drainage tube introducer according to the embodiment of the present invention are shown in FIGS. 3 to 10.

Referring to the accompanying drawings, the drainage tube introducer according to the embodiment of the present invention includes an introducer body 30 formed in the standard size in which an operator may grip the introducer body by one hand, a pin assembly 40, 50 inserted into an inner space 36 of the introducer body 30, and an elastic member 60 moving the pin assembly 40, 50 by using elastic energy.

The introducer body 30 has a predetermined length. A pin hole 32 and a pin insertion hole 34 are provided respectively at opposite ends of the introducer body 30 in a longitudinal direction thereof. The pin hole 32 is arranged at a distal end of the introducer body 30 and the pin insertion hole 34 is arranged at a proximal end of the introducer body 30. The inner space 36 is provided long in the longitudinal direction of the introducer body 30 in the introducer body 30, wherein opposite ends of the inner space communicate with each of the pin hole 32 of the distal end and the pin insertion hole 34 of the proximal end. Accordingly, the pin hole 32 of the distal end and the pin insertion hole 34 of the proximal end communicate with each other through the inner space 36 therebetween. The introducer body 30 includes a stop hole 38, which communicates with the inner space 36, formed through an upper part of a circumference of a middle portion thereof.

The pin assembly 40, 50 is inserted through the pin insertion hole 34 into the inner space 36 of the introducer body 30. The pin assembly 40, 50 includes a pin 40 of a front part thereof (a distal end side thereof) and an operating lever 50 of a rear part thereof (a proximal end side thereof).

The pin 40 is introduced to the inner space 36 so as to move in forward/rearward directions relative to the pin hole 32. Accordingly, when the pin 40 moves forward, an introducing end portion 42 of the distal end side protrudes through the pin hole 32 to the outside, and contrarily, when the pin moves rearward, the introducing end portion 42 protruding through the pin hole 32 is withdrawn into the introducer body. The introducing end portion 42 may be configured to have a pointed end. The pin 40 includes a flange 44 provided on a rear portion thereof so as to enlarge an outer circumference of the pin 40. The drainage tube (see reference numerals 10, 22, 24) according to the embodiment of the present invention is fitted over an outer circumference of the introducing end portion 42 protruding through the pin hole 32 to the outside. That is, the introducing end portion 42 is fitted into the tube member 10 of the drainage tube (see reference numerals 10, 22, 24).

The distal end of the operating lever 50 is connected to an upper side of the rear portion of the pin 40. The operating lever 50 extends from the flange 44 so as to have an upward inclination and includes a stop block 52 inserted into the stop hole 38 when the pin 40 moves forward relative to the pin hole 32. The stop block 52 is arranged at a rear portion of the operating lever 50. Since the operating lever 50 made of an elastic material has a plate-shaped structure having a thin depth in upward/downward directions, the stop block is bent downward when the stop block 52 inserted into the stop hole 38 is pressed down. Accordingly, the stop block 52 may be released from the stop hole 38.

The stop block 52 includes a protruding part 54 convexly protruding through the stop hole 38 to the outside and a stopping part 56 provided at a rear portion of the protruding part 54.

The protruding part 54 is configured to protrude more at a middle portion thereof than at vicinities thereof such that the stop block 52 is inserted into and released from the stop hole 38 smoothly and naturally. The protruding part 54 may have a curved surface or an inclined surface configured such that the middle portion thereof protrudes more than the surrounding portions.

The stopping part 56 includes a first surface 56a being in contact with a rear portion of an inner circumference of the stop hole 38 and a second surface extending rearward from the first surface 56a and being in contact with a wall surface of the inner space 36 connected to the rear portion of the inner circumference of the stop hole 38.

The elastic member 60 applies a predetermined elastic force to the pin 40 in a direction (a direction in which the introducing end portion 42 protruding through the pin hole 32 is withdrawn into the introducer body) in which the pin 40 moves rearward relative to the pin hole 32. Preferably, a coil spring is used as the elastic member 60. While a coil spring as the elastic member 60 is fitted over the outer circumference of the pin 40 in the inner space 36, a first end part of the coil spring is supported by the wall surface constituting the inner space 36 at a side of the pin hole 32 and a second end part of the coil spring is supported by the flange 44. The elastic member 60 also functions to maintain holding performed by the stopping part 56. A reference numeral 46 denotes a position-fixing protrusion for a spring.

The drainage tube introducer according to the embodiment of the present invention further includes a sleeve 70 pressing the stop block 52, an insertion hole cover 80 covering the pin insertion hole 34 from the outside, and a cap 90 being fitted over a distal end side of the introducer body 30.

The sleeve 70 is fitted over an outer circumference of the introducer body 30 so as to move slidably thereon, is arranged so as to cover the stop hole 38, and includes a pressing protrusion 72 pressing the stop block 52 downward while being in contact with the protruding part 54 of the stop block 52 when the sleeve slides forward. Anti-migration protrusions 74 (a corrugated part) used when an operator slides the sleeve 70 are provided on an upper part of a circumference of the sleeve 70. The sleeve 70 may be made of a transparent or translucent material such that an operator may check the insertion or motion state of the stop block 52 by naked eye.

When the stop hole 38 is covered by the sleeve 70, the sleeve 70 prevents any access to the stop block 52 from an outside, so that the stop block 52 may be prevented from unintentionally being pressed by an external force.

The insertion hole cover 80 is separably combined with the proximal end of the introducer body 30. The insertion hole cover 80 may be configured to have a size (length) usable as a part gripped by an operator when the operator grips the introducer body 30 by using one hand.

Figure 10:
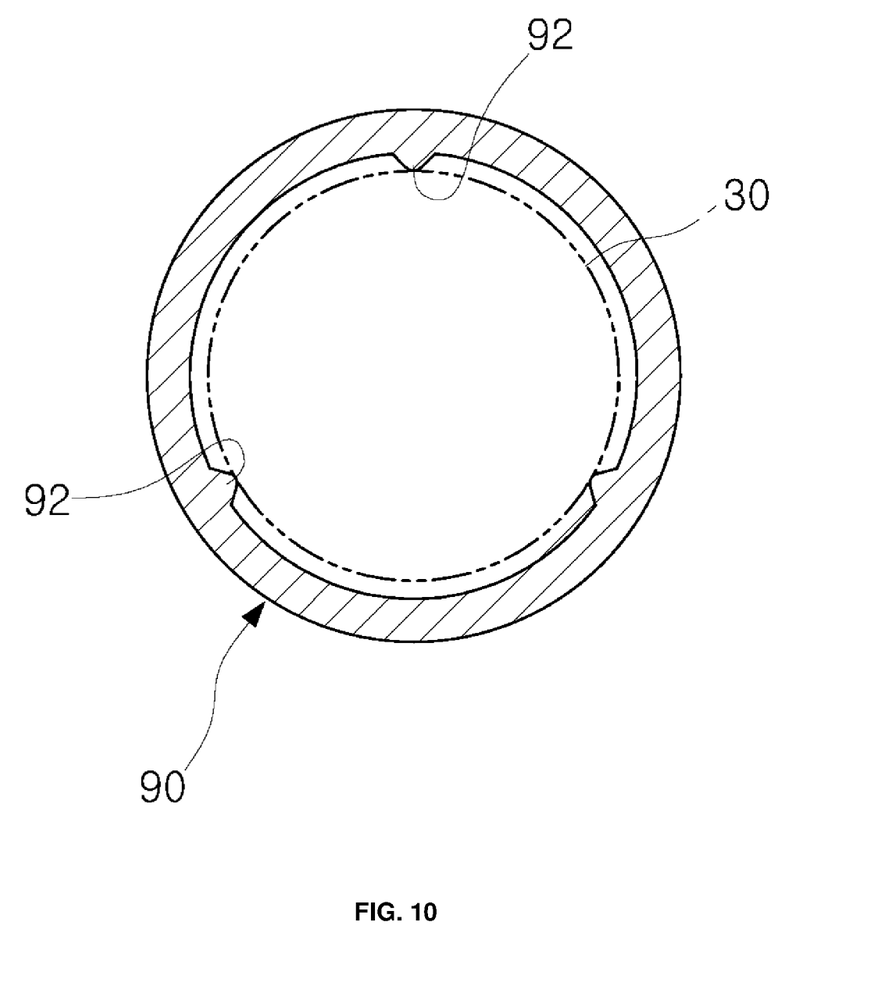
FIG. 10 is a cross-sectional view showing a cap shown FIGS. 3 and 5.

The cap 90 being fitted over the distal end side of the introducer body 30 protects from the outside the introducing end portion 42 protruding through the pin hole 32 to the outside from the inner space 36 and the drainage tube (see reference numerals 10, 22, 24) according to the embodiment of the present invention, the drainage tube being fitted over the outer circumference of the introducing end portion 42. The cap 90 includes a singular or plural locking protrusion 92 provided on an inner circumference thereof and being in close contact with an outer circumference of the distal end side of the introducer body 30 when the cap is fitted over the distal end side of the introducer body 30. The locking protrusion 92 may be configured to be long in a longitudinal direction of the cap.

The locking protrusion 92 may reduce friction (a force required to lock and separate the cap 90 to and from the introducer body) between the cap 90 and the introducer body 30 to a proper level so as to securely lock the cap 90 to the distal end side of the introducer body 30.

A reference numeral 110 denotes a pin guide guiding a movement of the pin 40 forward and rearward. The pin guide 110 includes a guide hole part 112 and a guide member 114. The guide hole part 112 is arranged behind the pin 40 in the inner space 36 and is configured to be long in forward/rearward directions on a lower part of the wall surface of the inner space 36. The distal end of the guide member 114 is connected to a lower side of the rear portion of the pin 40. The guide member 11 extends rearward from the flange 44 and includes a guide protrusion 116 inserted into the guide hole part 112.

The pin guide 110 may guide such that the pin assembly 40, 50 accurately moves forward/rearward and prevent an arrangement direction of the operating lever 50 from being changed by a rotation of the pin assembly 40, 50.

A reference numeral 120 denotes a position determination means determining a position of the sleeve 70 on the introducer body 30 such that the sleeve 70 moving slidably is positioned at a position to cover the stop hole 38. The position determination means 120 includes a holding groove part 122 concavely provided at a lower part of the circumference of the introducer body 30 and a holding protrusion 124 protruding to the lower part of the circumference of the introducer body 30 from the sleeve 70 so as to be inserted into and held in the holding groove part 122. The sleeve 70 may be configured to have an inner circumference so as to have a predetermined gap (an interval for holding and releasing) between the sleeve and the outer circumference of the introducer body 30 such that the holding protrusion 124 is smoothly and naturally held in and released from the holding groove part 122. In addition, a part on which the holding groove part 122 is in contact with the holding protrusion 124 each other may be configured to be a curved surface or an inclined surface.

The position determination means 120 allows the sleeve 70 to be maintained at a state arranged at a position covering the stop hole 38 so as to prevent misoperation of the sleeve 70.

A reference numeral 100 denotes a slide hole part. The slide hole part 100 is long provided forward from the holding groove part 122 at the lower part of the circumference of the introducer body 30 and is configured to have the same depth and width as or a depth and a width similar to a depth and a width of the holding groove part 122. When the sleeve 70 located at the position covering the stop hole 38 is moved forward, the holding protrusion 124 released from the holding groove part 122 is introduced into the slide hole part 100. The holding protrusion 124 moved to the slide hole part 100 from the holding groove part 122 acts as a slide protrusion so as to guide sliding of the sleeve 70 in cooperation with the slide hole part 100.

Figure 6:
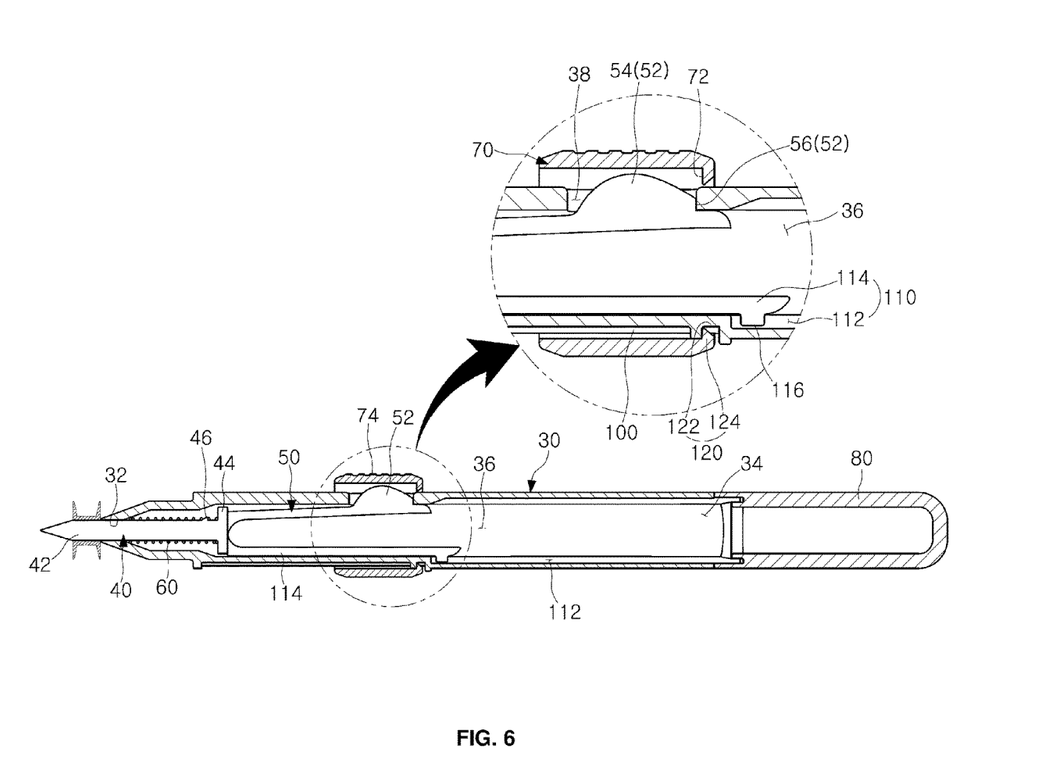
FIGS. 6 to 8 are cross-sectional views showing an inner structure and an operation process of the drainage tube introducer according to the embodiment of the present invention.
Figure 7:
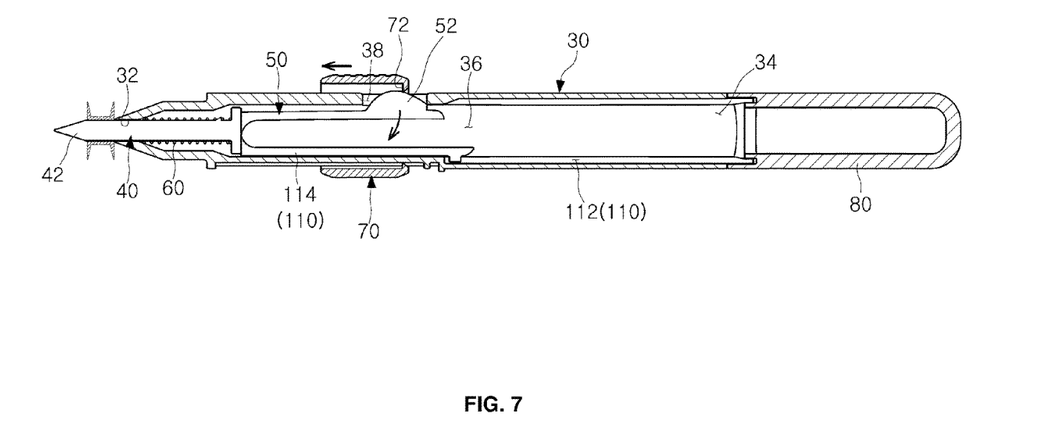
Figure 8:
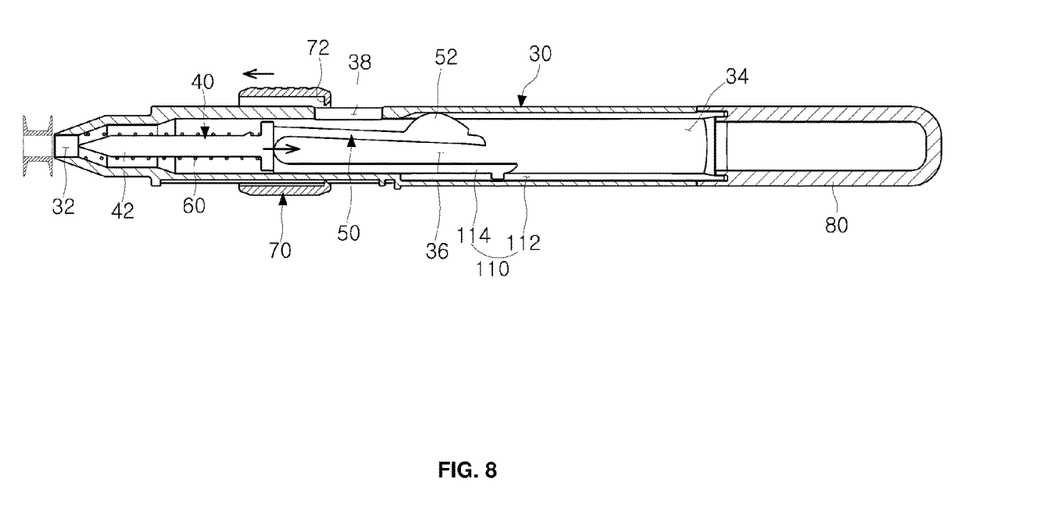
Figure 9:
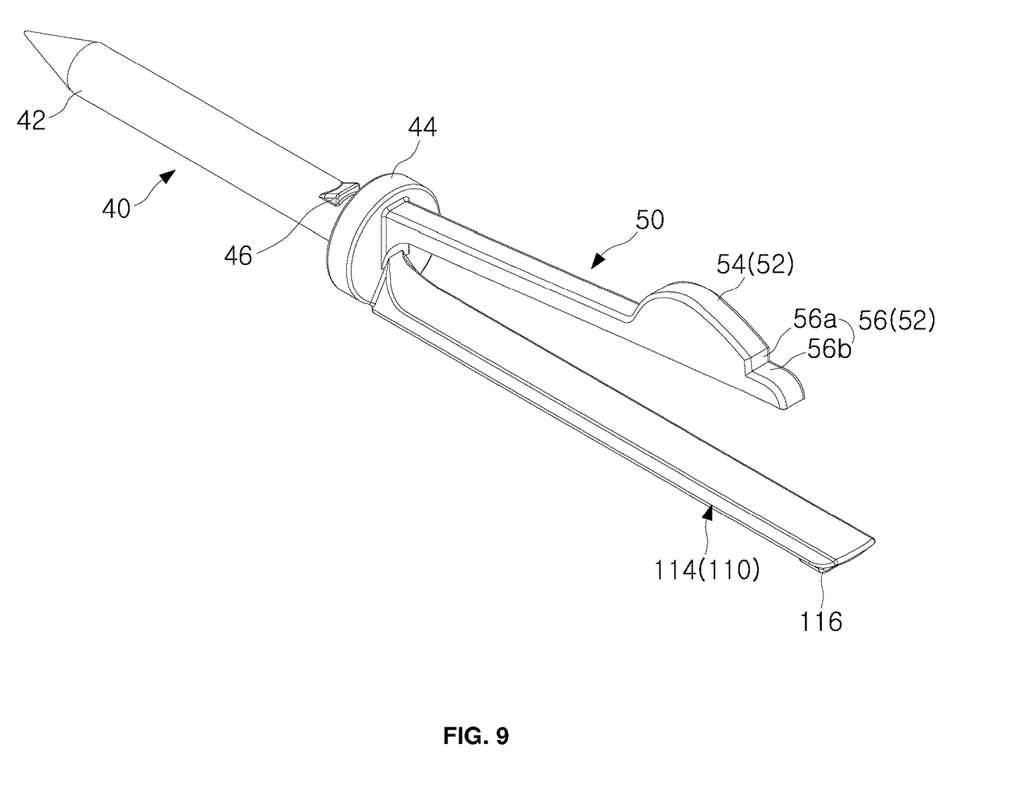
FIG. 9 is an enlarged view showing a pin assembly shown in FIG. 5.

According to the drainage tube introducer according to the embodiment of the present invention configured as described above, when the pin 40 moves forward, the introducing end portion 42 protrudes through the pin hole 32 to the outside, the protruding part 54 protrudes through the stop hole 38 to the outside, the stopping part 56 is held in the stop hole 38, and the coil spring as the elastic member 60 is compressed. When the sleeve 70 is pushed and slid forward by a thumb of one hand with which an operator grips the introducer body 30 while the sleeve 70 slides and is arranged at the position covering the stop hole 38 by the position determination means 120, the pin 40 is moved rearward and the introducing end portion 42 protruding through the pin hole 32 is withdrawn into the introducer body.

Particularly, in the operating lever 50, the stop block 52 is bent in a direction in which the stop block is released from the stop hole 38 by the pressing of the pressing protrusion 72 on the protruding part 54, the elastic member 60 is restored to an original state at a time at which the stop block 52 is released from the stop hole 38, and the pin 40 and the operating lever 50 are moved rearward by a restoring force of the elastic member 60. In this case, the drainage tube (see reference numerals 10, 22, 24) according to the embodiment of the present invention being fitted over the outer circumference of the introducing end portion 42 protruding through the pin hole 32 to the outside is separated from the introducing end portion 42 withdrawn through the pin hole 32 into the introducer body.

Figure 11:
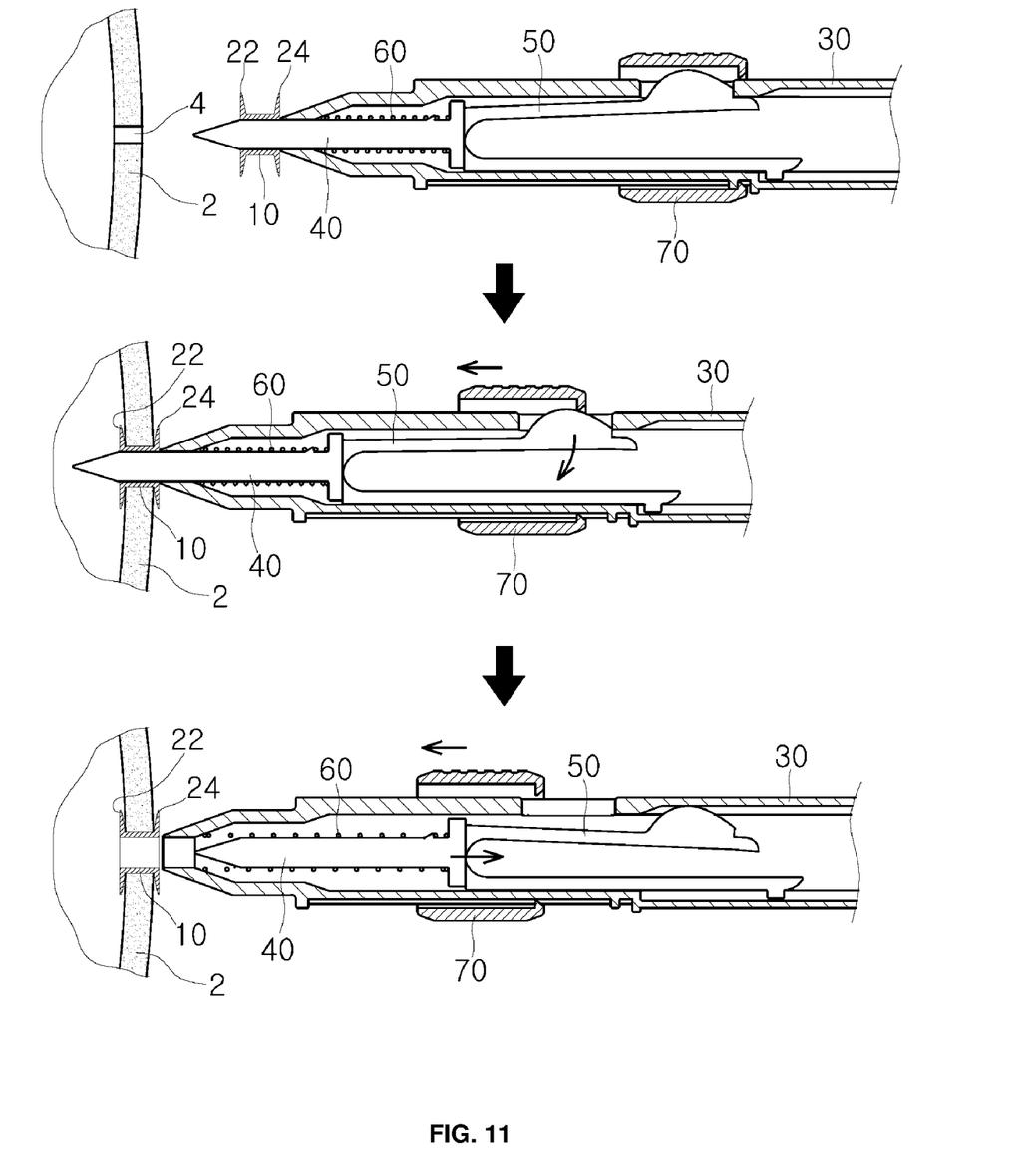
FIG. 11 shows a treatment process using the drainage tube and the drainage tube introducer according to the embodiment of the present invention.

An abscess treatment process using the drainage tube and the drainage tube introducer according to the embodiment of the present invention will be described referring to FIG. 11.

First, an outer wall of the infected abscess 2 is incised and the incision portion 4 is provided so as to insert the drainage tube into the infected portion 2. Next, the drainage tube is fitted over the outer circumference of the introducing end portion 42 protruding to the outside of the introducer body.

Next, while the drainage tube is fitted over the introducing end portion 42, the first wing member 22 is introduced through the incision portion 4 into the infected portion 2 in cooperation with the first end portion 12 of the tube member 10. For example, while a portion of the first wing member 22 is introduced into the infected portion, the entirety of the first wing member 22 may be introduced into the infected portion by rotating the drainage tube in cooperation with the drainage tube introducer. Of course, in this process, the introducing end portion 42 is also introduced into the infected portion.

Next, the pin 40 is moved rearward by sliding the sleeve 70 forward. Then, since the introducing end portion 42 protruding through the pin hole 32 is withdrawn into the introducer body, the drainage tube is separated from the introducing end portion 42 and accordingly, the introduction of the drainage tube is completed.

Next, an operator waits till the incision portion 4, which is a treatment portion, is recovered. When the treatment portion is recovered and the drainage slit corresponding to the outer circumference of the tube member 10 is formed at the treatment portion, the inserted drainage tube is removed from the treatment portion.

Although the preferred embodiment of the present invention have been described for illustrative purposes, those skilled in the art will appreciate that various modifications, additions and substitutions are possible, without departing from the scope and spirit of the invention as disclosed in the accompanying claims. In addition, the technical spirit described in the embodiment of the present invention may be embodied independently and in combination with each other.

What is claimed is:

1. A drainage tube introducer for operating on a Bartholin's duct abscess, the drainage tube introducer comprising:
an introducer body including a pin hole provided on a distal end thereof, an inner space communicating with the pin hole, and a stop hole formed through one side of a circumference of the introducer body, the stop hole communicating with the inner space;

a pin for inserting a drainage tube, the pin being introduced to the inner space so as to move forward/rearward relative to the pin hole, wherein when the pin moves forward, a pointed introducing end portion of a distal end side of the pin protrudes through the pin hole to an outside;

an operating lever, made of an elastic material, being connected to a rear portion of the pin for inserting the drainage tube and having a stop block inserted into the stop hole while the pin moves forward, and a protruding part provided at the stop block, the protruding part protruding through the stop hole to an outside, wherein when the stop block is pressed, the stop block is bent in a direction being released from the stop hole;

an elastic member applying an elastic force to the pin in a direction in which the pin moves rearward, and a sleeve for manipulating the pin, the sleeve being fitted over the outer circumference of the introducer body so as to move slidably thereon and arranged so as to cover the stop hole and having a pressing protrusion pressing the protruding part while being in contact with the protruding part when the sleeve slides, wherein the drainage tube is configured to be positioned over an outer circumference of the pointed introducing end portion protruding through the pin hole to the outside, is configured to be introduced through an incision portion into an infected portion in cooperation with the pointed introducing end portion, and is configured to be separated from the pointed introducing end portion when the stop block is released from the stop hole and the pin is moved rearward by the elastic member.

2. The drainage tube introducer of claim 1, wherein a middle portion of the protruding part is configured to protrude more than surrounding portions.

3. The drainage tube introducer of claim 1, wherein the stop block includes a stopping part provided on a rear portion thereof, the stopping part including a first surface being in contact with an inner circumference of the stop hole and a second surface extending rearward from the first surface and being in contact with a wall surface of the inner space.

4. The drainage tube introducer of claim 1, further comprising:
   a position determination means determining a position of the sleeve on the introducer body such that the sleeve is positioned at a position to cover the stop hole.

5. The drainage tube introducer of claim 1, further comprising:
   a pin guide guiding a movement of the pin forward and rearward.

6. The drainage tube introducer of claim 1, further comprising:
   an insertion hole cover being separably combined with a proximal end of the introducer body,
   wherein a pin insertion hole communicating with the inner space is provided at the proximal end of the introducer body.

7. The drainage tube introducer of claim 1, further comprising:
   a cap being fitted over a distal end side of the introducer body, the cap protecting the introducing end portion protruding through the pin hole to the outside and the drainage tube being fitted over the outer circumference of the introducing end portion.

* * * * *